United States Patent [19]

Nedelec et al.

[11] 4,318,910
[45] Mar. 9, 1982

[54] INDOLOBENZOXAZINES

[75] Inventors: Lucien Nedelec, Le Raincy; Andre Pierdet, Noisy-le-Sec; Claude Dumont, Nogent-sur-Marne, all of France

[73] Assignee: Roussel Uclaf, Paris, France

[21] Appl. No.: 246,169

[22] Filed: Mar. 23, 1981

[30] Foreign Application Priority Data

Apr. 3, 1980 [FR] France ................. 80 07544

[51] Int. Cl.³ ............... A01N 43/84; C07D 498/06
[52] U.S. Cl. .............................. 424/248.4; 544/99
[58] Field of Search ................. 544/99; 424/248.4

[56] References Cited

U.S. PATENT DOCUMENTS 4,238,486 12/1980 Jones ........................ 424/248.4

OTHER PUBLICATIONS

Kornfeld et al., Journ. Amer. Chem. Soc. 78, 3087-3114, pp. 3091, 3094, and 3103.

Primary Examiner—Ethel G. Love
Attorney, Agent, or Firm—Hammond & Littell, Weissenberger and Muserlian

[57] ABSTRACT

Novel indolobenzoxazines of the formula

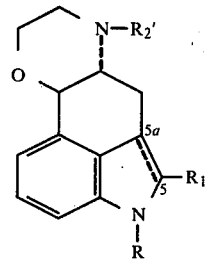

I' wherein R is selected from the group consisting of hydrogen, alkyl of 1 to 5 carbon atoms and optionally substituted aralkyl of 7 to 12 carbon atoms, $R_1$ is selected from the group consisting of hydrogen, chlorine and bromine, $R_2'$ is selected from the group consisting of hydrogen, optionally substituted alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and the dotted line between 5 and 5a indicates the optional presence of a double bond and their non-toxic, pharmaceutically acceptable acid addition salts having hypotensive, antihypertensive and dopaminergic agonist properties and a process for their preparation.

15 Claims, No Drawings

INDOLOBENZOXAZINES

OBJECTS OF THE INVENTION

It is an object of the invention to provide the novel products of formula I' and their non-toxic, pharmaceutically acceptable acid addition salts and their preparation.

It is a further object of the invention to provide novel hypotensive and dopaminergic agonist compositions and to provide a novel method of inducing hypotensive and dopaminergic agonist activity in warm-blooded animals.

These and other objects and advantages of the invention will become obvious from the following detailed description.

THE INVENTION

The novel compounds of the invention are selected from the group consisting of indolobenzoxazines of the formula

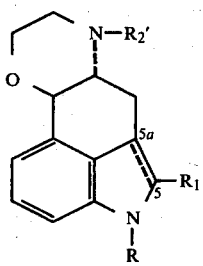

I' wherein R is selected from the group consisting of hydrogen, alkyl of 1 to 5 carbon atoms and optionally substituted aralkyl of 7 to 12 carbon atoms, $R_1$ is selected from the group consisting of hydrogen, chlorine and bromine, $R_2'$ is selected from the group consisting of hydrogen, optionally substituted alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and the dotted line between 5 and 5a indicates the optional presence of a double bond and their non-toxic, pharmaceutically acceptable acid addition salts.

Among the preferred compounds of the invention are compounds of the formula

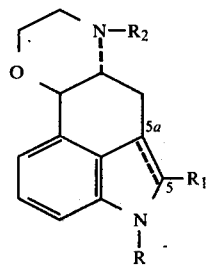

I wherein R, $R_1$ and the dotted line have the above meanings and $R_2$ is selected from the group consisting of hydrogen, alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts. Particularly preferred compounds of formula I are those wherein a double bond is present at the 5,5a position.

In the compounds of formulae I and I', examples of alkyl of 1 to 5 carbon atoms are methyl, ethyl, propyl, isopropyl, butyl, sec.-butyl, tert.-butyl and pentyl and the alkyl groups may be substituted with hydroxy or a halogen such as chlorine or bromine. Examples of aralkyl of 7 to 12 carbon atoms are benzyl and phenethyl and the optional substituents include chlorine, bromine, methyl, ethyl, methoxy, $CF_3-$ and $CH_3S-$. Examples of cycloalkylalkyl of 4 to 7 carbon atoms are cyclopropylmethyl and cyclobutylmethyl. Examples of alkenyl and alkynyl of 3 to 7 carbon atoms are allyl, buten-2-yl and propargyl.

Examples of acids for the non-toxic, pharmaceutically acceptable acid addition salts are inorganic acids such as hydrochloric acid, hydrobromic acid, hydroidic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkanesulfonic acids such as methanesulfonic acid and ethanesulfonic acid, arylsulfonic acids such as benzene sulfonic acid and p-toluenesulfonic acid and arylcarboxylic acids.

The dotted line in the morpholino ring indicates that the junction between the morpholino ring and the cyclohexane ring is trans. It is to be understood that racemic mixtures as well as their corresponding optically active isomers are included within the scope of the invention.

Among the preferred compounds of formula I are those wherein R is hydrogen, those wherein $R_2$ is selected from the group consisting of hydrogen, alkyl of 1 to 5 carbon atoms and cycloalkylalkyl of 4 to 7 carbon atoms, those wherein $R_1$ is hydrogen or bromine and those wherein $R_2$ is selected from the group consisting of hydrogen and alkyl of 1 to 5 carbon atoms and their non-toxic, pharmaceutically acceptable acid addition salts.

The novel process of the invention for the preparation of compounds of formula I' comprises reducing a compound of the formula

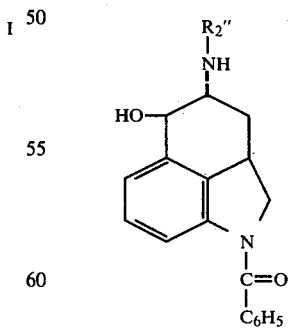

II wherein $R_2''$ is selected from the group consisting of hydrogen, alkyl of 1 to 5 carbon atoms, cycloalkylalkyl of 4 to 7 carbon atoms and optionally substituted aralkyl of 7 to 12 carbon atoms to obtain a compound of the formula

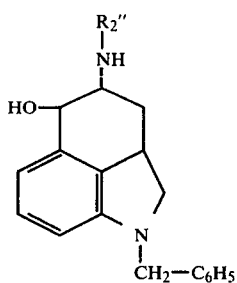

reacting the latter with chloroacetyl chloride to obtain a compound of the formula

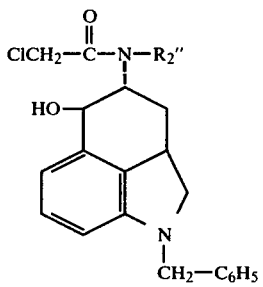

cyclizing the latter to obtain a compound of the formula

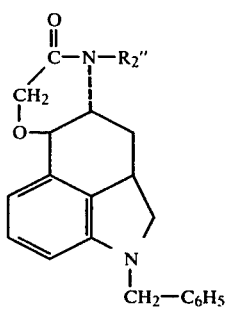

reducing the latter to obtain a compound of the formula

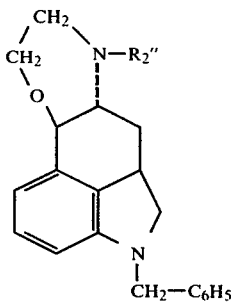

which is a compound of formula I' wherein $R_2'$ is $R_2''$, $R_1$ is hydrogen, R is benzyl and a single bond is in the 5,5a-position and (a) when $R_2''$ is hydrogen, reacting the latter with a halide of the formula Hal—$R_2'''$    VI wherein Hal is chlorine, bromine or iodine and $R_2'''$ is $R_2'$ other hydrogen and haloalkyl to obtain a compound of the formula

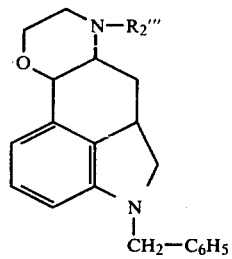

which is a compound of formula I' wherein $R_2'$ is $R_2'''$, $R_1$ is hydrogen, R is benzyl and a single bond is in the 5,5a-position and, if desired, when $R_2'''$ is hydroxyalkyl reacting the latter with a halogenation agent to obtain a compound of the formula

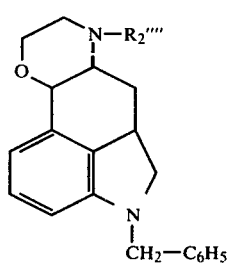

which is a compound of formula I' wherein $R_2'$ is $R_2''''$, $R_2''''$ represents a haloalkyl, $R_1$ is hydrogen, R is benzyl and a single bond is in 5,5a-position (b) or when $R_2''$ is hydrogen, reacting a compound of formula $I_{C'}$ with a methylation agent to obtain a compound of the formula

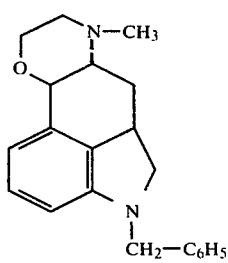

which is a compound of formula I' wherein $R_2'$ is methyl, $R_1$ is hydrogen, R is benzyl and a single bond is in the 5,5a-position and, if desired, the compounds of formulae $I_{A'}$, $I_{B'}$, $I_{C'}$ and $I_{B''}$ are subjected to hydrogenolysis to obtain a compound of the formula

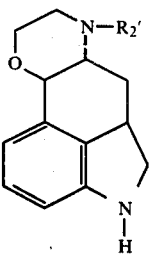

which is a compound of formula I' wherein $R_2'$ has the above definition and R and $R_1$ are hydrogen and a single bond is in the 5,5a-position which may be recovered or reacted with a halide of the formula Hal—R'  VII wherein Hal is chlorine, bromine or iodine and R' is alkyl of 1 to 5 carbon atoms and optionally substituted aralkyl of 7 to 12 carbon atoms to obtain a compound of the formula

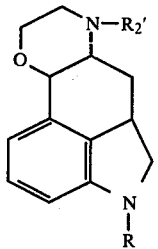

$I_D''$ or subjecting a compound of formula $I_D'$ to a deshydrogenation to obtain a compound of the formula

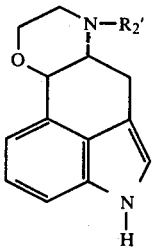

$I_E'$ which is a compound of formula I' wherein $R_2'$ has the above definition, R and $R_1$ are hydrogen and a double bond is in the 5,5a-position, which, if desired, may be isolated or treated with a halogenation agent to obtain a compound of the formula

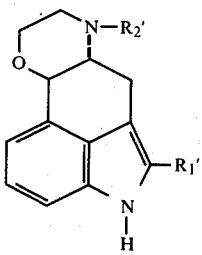

$I_F'$ which is a compound of formula I' wherein $R_1'$ is chlorine or bromine, $R_2'$ has the above definition, $R_1$ is $R_1'$, R is hydrogen and a double bond is in the 5,5a-position or reacting a compound of formula $I_E'$ with a halide of formula VII to obtain a compound of the formula

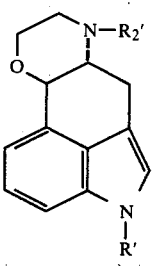

$I_G'$ which is a compound of formula I' wherein R' and $R_2'$ have the above definition, $R_1$ is hydrogen, R is R' and a double bond is in the 5,5a-position which may be isolated or reacted with a halogenation agent to obtain a compound of the formula

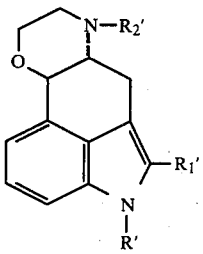

$I_H'$ which is a compound of formula I' wherein $R_1$ is $R_1'$, R is R', $R_2'$ has the above definition and a double bond is in the 5,5a-position and any of the products of formulae $I_A'$, $I_B'$, $I_C'$, $I_D'$, $I_B''$, $I_D''$, $I_E'$, $I_F'$, $I_G'$ or $I_H'$ maybe salified with an acid.

The reduction of the compound of formula II is preferably effected with a metallic halide, especially lithium aluminum hydride in the presence of a Lewis acid, especially aluminum chloride and the reduction is effected in a solvent such as dimethoxyethane or other ethers such as tetrahydrofuran or dioxane, preferably the latter. The condensation of the compound of formula III with chloroacetyl chloride is preferably effected in the presence of a fixation agent for acids, preferably sodium hydroxide, in an organic solvent such as dioxane or tetrahydrofuran, but most preferably in chloroform.

The cyclization of the compound of formula IV is effected with a strong base such as an alkali metal hydroxide such as sodium hydroxide or potassium hydroxide; an alkali metal alcoholate such as sodium ethylate or sodium tert.-butylate but is preferably sodium hydride and is preferably in an ether like dioxane or tetrahydrofuran and especially dimethoxyethane. The reduction of the compound of formula V is effected with a metallic hydride especially lithium aluminum hydride in an ether, especially refluxing tetrahydrofuran.

The halide of formula VI may be a chloride or bromide, but especially an iodide and the reaction is advantageously effected with a secondary amine of formula $I_A'$ wherein $R_2''$ is hydrogen in the presence of an acid fixation agent such as an alkali metal carbonate such as potassium carbonate in a solvent such as dimethylformamide. The halogenation agent for reacting with the product of formula I$_B'$ is preferably a chlorination agent such as methane sulfonyl chloride.

The methylation leading to the compounds of formula I$_C'$ may be effected with a mixture of formic aldehyde and formic acid but preferably is effected with formic aldehyde in the presence of a reducing agent such as sodium cyanoborohydride and acetonitrile is the preferred solvent. The hydrogenolysis of the compounds of formulae I$_A'$, I$_B'$, I$_B''$ or I$_C'$ may be effected with hydrogen in the presence of a catalyst such as Raney nickel, palladized strontium carbonate or palladium hydroxide but preferably in the presence of palladized activated carbon or palladized talc.

The deshydrogenation of the compound of formula I$_D'$ may be effected with acceptors of hydride ions such as cinnamic acid or maleic anhydride or cupric chloride preferably manganese dioxide in the optional presence of a catalyst such as Raney nickel or palladium but the deshydrogenation is preferably effected with methylene chloride. The halogenation agent for reacting with a compound of formula I$_D'$ or I$_E'$ may be N-chlorosuccinimide for chlorination or N-bromo-succinimide for bromination or preferably a bromine-pyrrolidone complex of the formula

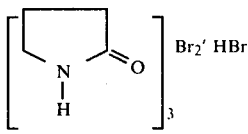

The halide of formula VII is preferably an iodide and the reaction is effected in the presence of an acid fixation agent such as an alkali metal carbonate or hydroxide such as sodium carbonate or potassium hydroxide.

In the compounds of formulae II, III and IV, the dotted line indicates the —OH and amino group are in the trans position.

The compounds of formula I' are basic and may be salified with an acid in approximately stoichiometric amounts to form the acid addition salts which can be done without isolating the free base. The racemates of formula I' may be resolved into their optically active enantiomers by known methods such as the formation of salts with optically active acids.

The compounds of formula II may be prepared by effecting a Neber rearrangement [Chem. Rev., Vol. 64 (1964), page 81] with a tosyloxime of the formula

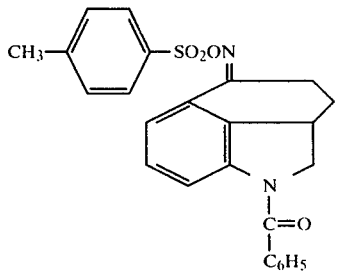

described in J.A.C.S., Vol. 78 (1965), p. 3087 and then reducing the amino ketone obtained for example with sodium borohydride to obtain a compound of the formula

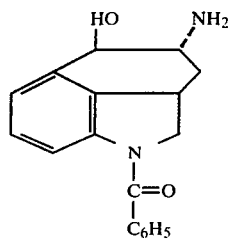

which is a compound of formula II wherein R$_2''$ is hydrogen which, if desired, may be reacted with trifluoroacetic anhydride preferably in the presence of a base such as an alkali metal hydroxide to obtain a compound of the formula

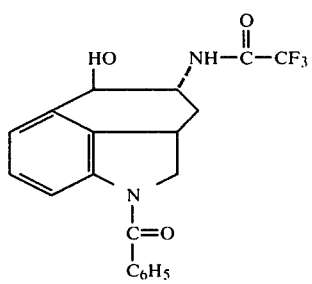

and reacting the latter with an alkaline agent such as alkali metal carbonate or hydroxide or a tertiary amine with a halide of the formula Hal—R$_3$   XI wherein Hal has the above definition and R$_3$ is R$_2''$ except hydrogen to obtain a compound of the formula

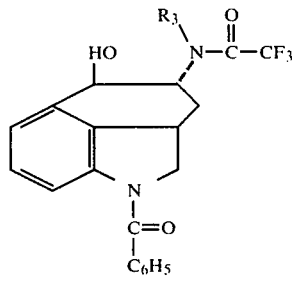

and reacting the latter with an agent capable of selective hydrolysis of the trifluoroacetamido group such as sodium carbonate to obtain the corresponding compound of formula II.

The novel hypotensive and dopaminergic agonist compositions of the invention are comprised of an hypotensively and dopaminergic agonistically effective amount of at least one compound of formula I' and their non-toxic, pharmaceutically acceptable acid addition salts and an inert pharmaceutical carrier. The compositions may be in the form of tablets, dragees, gelules, granules, suppositories and injectable solutions or suspensions.

Examples of suitable pharmaceutical carriers are talc, arabic gum, lactose, starch, magnesium stearate, cacao butter, fatty bodies of animal or vegetable origin, aqueous and non-aqueous vehicles, paraffinic derivatives, glycols, diverse wetting agents, dispersants or emulsifiers and preservatives.

The compositions are useful for the treatment of neurological syndromes of extra-pyramidal origin such as for the treatment of Parkinson disease and the treatment of post-encephalitic parkinson syndromes. They are also useful for the treatment of prolactin hypersecretion by antehypophysis such as for the treatment of hypogonadism in the male or female. They are also useful for the treatment of cerebral senescence or manifestation of a cerebral hypoxia.

Due to their hypotensive and antihypertensive activity, the compositions are useful for the treatment of essential arterial hypertension, hypertension of the fifties, of menopause, of diabetics, of obesity and of plethoria as well as for the treatment of arterial hypertension due to old age, of artherosclerosis and for the treatment of hypertension of renal origin.

Among the preferred compositions of the invention are those containing a compound of formula I, especially those wherein R is hydrogen, those wherein $R_2$ is hydrogen, alkyl of 1 to 5 carbon atoms or cycloalkylalkyl of 4 to 7 carbon atoms and their non-toxic, pharmaceutically acceptable acid addition salts. More preferred compositions are those of formula I wherein $R_1$ is hydrogen or bromine and $R_2$ is hydrogen or alkyl of 1 to 5 carbon atoms and their non-toxic, pharmaceutically acceptable acid addition salts.

The novel method of the invention of inducing hypotensive and dopaminergic agonist activity in warm-blooded animals, including humans, comprises administering to animals an amount of at least one compound of formula I' and their non-toxic, pharmaceutically acceptable acid addition salts sufficient to cause hypotensive and dopaminergic agonist activity. The compounds may be administered orally, rectally or parenterally and the usual daily dose will vary depending on the condition being treated, the specific compound and the method of administration. The usual daily oral dose is 0.002 to 1 mg/kg of compound of example 9 for the treatment of Parkinson disease.

In the following examples there are described several preferred embodiments to illustrate the invention. However, it should be understood that the invention is not intended to be limited to the specific embodiments.

EXAMPLE 1

5,5a,6,6a(RS),7,8,9,10a(RS)-octahydro-4-benzyl-7H-indolo-[3,4-g,h][1,4]-benzoaxazine

STEP A:
4-amno-1-benzoyl-1,2,2a,3,4(RS),5(RS)-hexahydro-benz-[c,d]-indol-5-ol A solution of 430 mg of 98% potassium and 20 ml of ethanol was added at 0° C. to a solution of 4.46 g of (p-methylphenyl-sulfonyl)-oxime of 1,2,2a,3,4(RS),5(RS)-hexahydro-benz[c,d]-indol-5-one in 20 ml of ethanol and 20 ml of chloroform and the mixture was stirred overnight at 0° C. The mixture was evaporated to dryness under reduced pressure and the residue was added to 200 ml of ether. The mixture was extracted with 2 N aqueous hydrochloric acid and the decanted aqueous phase was evaporated to dryness under reduced pressure. The residue was taken up several times in ethanol and evaporated to dryness under reduced pressure. A solution of 1.25 g of 95% sodium borohydride in 25 ml of ethanol was added dropwise with stirring at 0° C. to a mixture of 3.8 g of 4-amino-1-benzyl-1,2,2a,3,4(RS),5(RS)-hexahydro-benz-[c,d]-indol-5-one in 80 ml of ethanol and after one hour, the temperature returned to 22° C. After one hour at 22° C., a few ml of water and then 25 ml of 2 N sodium hydroxide solution were added to the mixture which was then extracted with chloroform. The organic phase was washed with water, dried and evaporated to dryness under reduced pressure to obtain 1.8 g of 4-amino-1-benzoy-1,2,2a,3,4(RS),5(RS)-hexahydro-benz-[c,d]-indol-5-ol melting at 173° C. after crystallization from methylene chloride.

STEP B:
4-amino-1,2,2a,3,4(RS),5(RS)-hexahydro-1-benzyl-benz-[c,d]-indol-5-ol 26 g of 4-amino-1-benzoyl-1,2,2a,3,4(RS),5(RS)-hexahydro-benz-[c,d]-indol-5-ol were slowly added with stirring under an inert atmosphere to a mixture of 26 g of lithium aluminum hydride, 13 g of aluminum chloride and 800 ml of dioxane and the mixture was refluxed for 2 hours and was cooled to 0° C. 300 of tetrahydrofuran containing 20% of water and 300 ml of 2 N sodium hydroxide solution were added dropwise to the mixture which was then vacuum filtered. The filter was washed with methylene chloride and the filtrate was added to 1.5 liters of methylene chloride. The organic phase was washed with water, dried and evaporated to dryness to obtain 20 g of 4-amino-1,2,2a,3,4(RS),5(RS)-hexahydro-1-benzyl-benz-[c,d]-indol-5-ol which melted at 166° C. after crystallization from methylene chloride.

STEP C:
2-chloro-N-[5-hydroxy-1-benzyl-1,2,2a,3,4(RS)-hexahydro-4-benz-[c,d]-indol]-acetamide A solution of 26 g of sodium hydroxide in 200 ml of water was added to a stirred mixture of 26 g of the product of Step B in 800 ml of chloroform and 14.8 ml of chloroacetyl chloride were added thereto dropwise. The mixture was stirred for 90 minutes and water was added thereto. The mixture was extracted with chloroform and the organic phase was washed with water, dried and evaporated to dryness under reduced pressure. A few ml of ether were added to the residue and the mixture was vacuum filtered. The product was dried under reduced pressure to obtain 29.5 g of 2-chloro-N-[5-hydroxy-1-benzyl-1,2,2a,3,4(RS)-hexahydro-4-benz-[c,d]-indol]-acetamide melting at 211° C.

STEP D:
4,5,5a,6,6a(RS),7,9,10a(RS)-octahydro-4-benzyl-8H-indolo-[3,4-g,h][1,4]-benzoxazine-8-one A solution of 356 mg of the product of Step C in 35 ml of dimethoxyethane was slowly added with stirring under an inert atmosphere to a mixture of 27.5 mg of sodium hydride and 2 ml of dimethoxyethane and after stirring for one hour, the mixture was poured into 50 ml of water. The mixture was extracted with methylene chloride and the organic phase was washed with water, dried and evaporated to dryness under reduced pressure to obtain 260 mg of 4,5,5a,6,6a(RS),7,9,10a(RS)-octahydro-4-benzyl-8H-indolo-[3,4-g,h][1,4]-benzoxazine-8-one melting at 260° C.

STEP E:
5,5a,6,6a(RS),7,8,9,10a(RS)-octahydro-4-benzyl-7H-indolo-[3,4-g,h][1,4]-benzoxazine 1 g of the product of Step D was added portion wise under an inert atmosphere to a stirred mixture of 1 g of lithium aluminum hydride in 100 ml of tetrahydrofuran and the mixture was refluxed for one hour and then was cooled in an ice-methanol bath. 50 ml of tetrahydrofuran containing 20% of water were added dropwise to the mixture which was then filtered. The filter was washed with tetrahydrofuran and then with methylene chloride. The decanted organic phase was washed with water, dried and evaporated to dryness under reduced pressure. The residue was chromatographed over silica gel and was eluted with a 95-5 chloroform-methanol mixture to recover the fraction with an Rf=0.3. The 684 mg of 5,5a,6,6a(RS),7,8,9,10a(RS)-octahydro-4-benzyl-7H-indolo-[3,4-g,h][1,4]-benzoxazine melted at 130° C. after crystallization from ether.

EXAMPLE 2

5,5a,6,6a(RS),7,8,9,10a(RS)-octahydro-4H-indolo-[3,4-g,h][1,4]benzoxazine

A mixture of 8 g of the product of Example 1, 2 g of 10% palladized carbon and 100 ml of pure acetic acid was stirred while bubbling hydrogen therethrough for 90 minutes and the mixture was then filtered. The filter was rinsed with acetic acid and the filtrate was evaporated to dryness under reduced pressure. The residue was added to 250 ml of water and the cooled mixture was made alkaline by addition of sodium hydroxide. The mixture was extracted with methylene chloride and the organic phase was washed with water, was dried and evaporated to dryness under reduced pressure. The residue was chromatographed over silica gel and was eluted with a 95-5 chloroform-methanol mixture to recover 4.75 g of the fraction with an Rf=0.2. The product was crystallized from methanol to obtain 5,5a,6,6a(RS),7,8,9,10a(RS)-octahydro-4H-indolo-[3,4-g,h][1,4]-benzoxazine melting at 128° C. and 158° C.

EXAMPLE 3

4,6,6a(RS),8,9,10a(RS)-hexahydro-7H-indolo-[3,4-g,h][1,4]-benzoxazine hydrochloride A mixture of 4.4 g of the product of Example 2, 17.6 g of activated manganese dioxide and 250 ml of methylene chloride was stirred under an inert atmosphere for 90 minutes and was then filtered. The filter was washed with methylene chloride and the filtrate was evaporated to dryness under reduced pressure. The 4.2 g of resin were chromatographed over silica gel and were eluted with a 92-5-3 ethyl acetate-methanol-ammonium hydroxide mixture to obtain 1.3 g of 4,6,6a(RS),8,9,-10a(RS)-hexahydro-7H-indolo-[3,4-g,h][1,4]-benzoxazine melting at 110° C.

2.38 g of the said base were dissolved in 50 ml of methylene chloride and 5 ml of 3 N hydrochloric acid were added to the cooled mixture which was then vacuum filtered. The product was washed with methylene chloride and was dried to obtain 2.25 g of 4,6,6a(RS),8,9,10a(RS)-hexahydro-7H-indolo-[3,4-g,h][1,4]-benzoxazine hydrochloride which was crystallized from methanol to obtain 1.98 g of 4,6,6a(RS),8,9,-10a(RS)-hexahydro-7H-indolo-[3,4-g,h][1,4]-benzoxazine hydrochloride melting at >250° C.

Analysis: $C_{13}H_{15}N_2OCl$; molecular weight=250.7; Calculated: %C, 62.28; %H, 6.03; %N, 11.17; %Cl, 14.14. Found: %C, 62.4; %H, 6.1; %N, 11.2; %Cl, 14.2.

EXAMPLE 4

5,5a,6,6a(RS),7,8,9,10a(RS)-octahydro-4-benzyl-7-methyl-4H-indolo-[3,4-g,h][1,4]-benzoxazine 10 g of the product of Example 1 were dissolved with stirring under an inert atmosphere in 200 ml of acetonitrile near 50° C. and after cooling the solution, 19.6 ml of 30% aqueous formic acid and then 3.27 g of sodium cyanoborohydride were slowly added thereto. The mixture was stirred for one hour and was then evaporated to dryness under reduced pressure. 500 ml of water were added and the mixture was extracted with methylene chloride. The organic phase was washed with water, dried and evaporated to dryness under reduced pressure. The residue was chromatographed over silica gel and was eluted with a 95-5 chloroform-methanol mixture to obtain 10.2 g of the fraction with an Rf=0.5. The resin was crystallized from isopropyl ether to obtain 9 g of 5,5a,6,6a(RS),7,8,9,10a(RS)-octahydro-4-benzyl-7-methyl-4H-indolo-[3,4-g,h][1,4]-benzoxazine melting at 106° C.

EXAMPLE 5

5,5a,6,6a(RS),7,8,9,10a(RS)-octahydro-7-methyl-4H-indolo-[3,4-g,h][1,4]-benzoxazine Hydrogen was bubbled through a mixture of 9 g of the product of Example 4, 2.25 g of 10% palladized carbon and 150 ml of acetic acid for 80 minutes and the mixture was filtered. The filter was rinsed several times with acetic acid and the filtrate was dried under reduced pressure. Water was added to the product and then cooled mixture was made alkaline with sodium hydroxide. The mixture was extracted with ethyl acetate and the organic phase was washed with water, dried and evaporated to dryness under reduced pressure. The residue was chromatographed over silica gel and was eluted with a 95-5 chloroform-methanol mixture to recover 4.9 g of 5,5a,6,6a(RS),7,8,9,10a(RS)-octahydro-7-methyl-4H-indolo-[3,4-g,h][1,4]-benzoxazine with an Rf=0.3. After crystallization from isopropyl ether, the product melted at 135° C., then 148° C.

EXAMPLE 6

6,6a(RS),7,8,9,10a(RS)-hexahydro-7-methyl-4H-indolo-[3,4-g,h][1,4]-benzoxazine hydrochloride A mixture of 5.2 g of the product of Example 5, 20.2 g of activated manganese dioxide and 250 ml of methylene chloride was stirred overnight under an inert atmosphere and was then filtered. The product was rinsed with methylene chloride and dried under reduced pressure. The residue of 5 g was chromatographed over silica gel and was eluted with a 95-5 chloroform-methanol mixture to obtain 3.4 g of 6,6a(RS),7,8,9,-10a(RS)-hexahydro-7-methyl-4H-indolo-[3,4-g,h][1,4]-benzoxazine melting at 216° C.

A solution of 3.4 g of the said base in 100 ml of methylene chloride was admixed with 10 ml of 2 N hydrogen chloride in ether and the mixture was vacuum filtered. The product was washed with methylene chloride and was dried to obtain 3.65 g of raw product. The latter was crystallized from ethanol to obtain 3.03 g of 6,6a(RS),7,8,9,10a(RS)-hexahydro-7-methyl-4H-indolo-[3,4-g,h][1,4]-benzoxazine hydrochloride melting at 22 250° C.

Analysis: $C_{14}H_{17}N_2OCl$; molecular weight=264.75; Calculated: %C, 63.51; %H, 6.47; %N, 10.58; %Cl, 13.39. Found: %C, 63.6; %H, 6.5; %N, 10.5; %Cl, 13.5.

EXAMPLE 7

5,5a,6,6a(RS),7,8,9,10a(RS)-octahydro-4-benzyl-7-methyl-4H-indolo-[3,4-g,h][1,4]-benzoxazine 9.11 g of potassium carbonate and 14.2 ml of propyl iodide were added with stirring under an inert atmosphere to a solution of 10 g of the product of Example 1 in 500 ml of dimethylformamide and the mixture was stirred at 50° C. for 3 hours, was cooled and was poured into 1.5 liters of water. The mixture was extracted with ether and the ether phase was washed with water, dried and evaporated to dryness under reduced pressure. The residue was chromatographed over silica gel and eluted with a 1-1 benzene-ethyl acetate mixture to obtain 8.9 g of 5,5a,6,6a(RS),7,8,9,10a(RS)-octahydro-4-benzyl-7-methyl-4H-indolo-[3,4-g,h][1,4]-benzoxazine which after crystallization from isopropyl ether melted at 105° C.

EXAMPLE 8

5,5a,6,6a(RS),7,8,9,10a(RS)-octahydro-7-propyl-4H-indolo-[3,4-g,h][1,4]-benzoxazine Hydrogen was bubbled through a stirred mixture of 8.75 g of the product of Example 7, 2.2 g of 10% palladized carbon and 100 ml of acetic acid for 90 minutes and the mixture was filtered. The filter was rinsed with acetic acid and the filtrate was evaporated to dryness. The residue was added to 150 ml of water and the cooled mixture was made alkaline with sodium hydroxide and was extracted with methylene chloride. The organic phase was washed with water, dried and evaporated to dryness under reduced pressure. The residue was chromatographed over silica gel and was eluted with a 95-5 chloroform-methanol mixture to obtain 6.5 g of 5,5a,6,6a(RS),7,8,9,10a(RS)-octahydro-7-propyl-4H-indolo-[3,4-g,h][1,4]-benzoxazine with an Rf=0.3. The product was crystallized from isopropyl ether to obtain 5.4 g of product melting at 85° C.

EXAMPLE 9

6,6a(RS),7,8,9,10a(RS)-hexahydro-7-propyl-4H-indolo-[3,4-g,h][1,4]-benzoxazine hydrochloride A mixture of 5.2 g of the product of Example 8, 20.8 g of activated manganese dioxide and 250 ml of methylene chloride was stirred under an inert atmosphere overnight and was then filtered. The filter was rinsed with methylene chloride and the filtrate was evaporated to dryness under reduced pressure. The residue of 5.02 g was chromatographed over silica gel and was eluted with a 95-5 chloroform-methanol mixture to obtain 3.18 g of 6,6a(RS),7,8,9,10a(RS)-hexahydro-7-propyl-4H-indolo-[3,4-g,h][1,4]-benzoxazine melting at 216° C.

A solution of the 3.18 g of base in 150 ml of methylene chloride was admixed with 10 ml of 2.5 N hydrogen chloride in ether and the mixture was vacuum filtered. The product was washed with methylene chloride and dried to obtain 3.65 g of raw product. The latter was crystallized from ethanol to obtain 2.56 g of 6,6a(RS),7,8,9,10a(RS)-hexahydro-7propyl-4H-indolo[3,4-g,h][1,4]-benzoxazine hydrochloride melting towards 240° C. (decomposition).

Analysis: $C_{16}H_{21}N_2OCl$; molecular weight=292.80; Calculated: %C, 65.63; %H, 7.23; %N, 9.57; %Cl, 12.11. Found: %C, 65.2; %H, 7.4; %N, 9.4; %Cl, 12.2.

EXAMPLE 10

5-bromo-7-propyl-6,6a(RS),7,8,9,10a(RS)-hexahydro-4H-indolo[3,4-g,h][1,4]-benzoxazine A solution of 8.1 g of pyrrolidine hydrotribromide in 2000 ml of dioxane was added with stirring under an inert atmosphere to a solution of 3 g of the free base of Example 9 in 250 ml of dioxane and the mixture was stirred for 30 minutes and was evaporated to dryness under reduced pressure. 250 ml of water were added to the residue and the mixture was extracted with methylene chloride. The organic phase was washed with aqueous sodium bicarbonate, then with water, dried and evaporated to dryness under reduced pressure. The residue of 3.8 g was chromatographed over silica gel and was eluted with a 95-5 chloroform-methanol mixture to obtain 2.7 g of 5-bromo-7-propyl-6,6a(RS),7,8,9,10a(RS)-hexahydro-4H-indolo[3,4-g,h][1,4]-benzoxazine with an Rf=0.55 and melting at >250° C.

A solution of the 2.7 g of base in 30 ml of methylene chloride was admixed with 10 ml of a solution of 2.5 N hydrogen chloride in ether and the mixture was vacuum filtered. The product was washed with methylene chloride and was dried and crystallized from ethanol to obtain 2.02 g of 5-bromo-7-propyl-6,6a(RS),7,8,9,10a(RS)-hexahydro-4H-indolo[3,4-g,h][1,4]-benzoxazine melting towards 275° C. with decomposition.

Analysis: $C_{16}H_{20}ClBrN_2O$; molecular weight=371.71; Calculated: %C, 51.69; %H, 5.42; %N, 7.54; %Cl, 9.54; %Br, 21.50. Found: %C, 51.9; %H, 5.6, %N, 7.6; %Cl, 9.3, %Br, 21.6.

EXAMPLE 11

6,6a(RS),7,8,9,10a(RS)-hexahydro-4,7-dimethyl-4H-indolo-[3,4-g,h][1,4]-benzoxazine oxalate 50 mg of sodium were added to 10 ml of liquid ammonia and 5 mg of $Fe_2(SO_4)_3.9H_2O$ were added thereto at −60° C. over 10 minutes with stirring. The mixture was stirred for 15 minutes and then a suspension of 0.228 g of the free base of Example 6 in 7 ml of ether were added thereto. The mixture was stirred for 5 minutes and then 0.15 ml of methyl iodide were added thereto. The temperature was allowed to rise to 20° C. and 10 ml of water were added thereto. The mixture was extracted with methylene chloride and the organic phase was washed with water, dried and evaporated to dryness to obtain 0.25 g of residue. The latter was chromatographed over silica gel and was eluted with 95-5 chloroform-methanol mixture to obtain 0.21 g of 6,6a(RS),7,8,9,10a(RS)-hexahydro-4,7-dimethyl-4H-indolo[3,4-g,h][1,4]-benzoxazine melting at 129° C.

A solution of 2.3 g of the said base in 40 ml of isopropanol was admixed with a mixture of 1.26 g of dehydrated oxalic acid in 20 ml of isopropanol and the mixture was vacuum filtered. The product was washed with ether to obtain 3.1 g of 6,6a(RS),7,8,9,10a(RS)-hexahydro-4,7-dimethyl-4H-indolo[3,4-g,h][1,4]-benzoxazine oxalate melting at 228° C.

Analysis: $C_{17}H_{20}O_5N_2$; molecular weight=332.356; Calculated: %C, 61.43; %H, 6.06; %N, 8.43. Found: %C, 61.6; %H, 6.1; %N, 8.6.

EXAMPLE 12

6,6a(RS),7,8,9,10a(RS)-hexahydro-5-bromo-7-methyl-4H-indolo-[3,4-g,h][1,4]-benzoxazine oxalate A solution of 8.15 g of pyrrolidone perbromide in 2000 ml of dioxane was slowly added to a solution of 2.5 g of the free base of Example 6 in 150 ml of dioxane and the mixture was stirred for 15 minutes and evaporated to dryness at room temperature. The residue was taken up in methylene chloride and the organic phase was washed with aqueous saturated sodium bicarbonate solution, dried and evaporated to dryness. The residue was chromatographed over silica gel and was eluted to obtain 2 g of 6,6a(RS),7,8,9,10a(RS)-hexahydro-5-bromo-7-methyl-4H-indolo-[3,4-g,h][1,4]-benzoxazine melting at >250° C.

A solution of 0.82 g of anhydrous oxalic acid in 10 ml of isopropanol was added to a solution of 2 g of the said free base in 40 ml of isopropanol and the mixture was vacuum filtered. The product was washed with isopropanol to obtain 2.5 g of 6,6a(RS),7,8,9,10a(RS)-hexahydro-5-bromo-7-methyl-4H-indolo-[3,4-g,h][1,4]-benzoxazine oxalate melting at >250° C.

IR Spectrum (nujol): Absorption region OH/NH; absorption at 1736, 1722 and 1697 cm$^{-1}$ (carbonyl); at 1614 cm$^{-1}$ (COO$^-$); at 1560, 1508 and 1490 cm$^{-1}$ (aromatic bands).

NMR Spectrum (DMSO): Peaks at 2.73 ppm(hydrogens of methyls); at 3.94 to 4.11 ppm (hydrogens of —N—CH$_2$O—); at 6.89 to 7.22 ppm (aromatic hydrogens).

EXAMPLE 13

5,5a,6,6a(RS),7,8,9,10a(RS)-octahydro-4-benzyl-7-(2-hydroxyethyl)-4H-indolo-[3,4-g,h][1,4]-benzoxazine 17 g of potassium carbonate were added with stirring under an inert atmosphere to a solution of 19 g of the product of Example 1 in 350 ml of dimethylformamide and 9.2 ml of bromoethanol were added thereto. The mixture was stirred for 2 hours at 50° C. and was cooled and and water was added thereto. The mixture was extracted with methylene chloride and the organic phase was washed with water, dried and evaporated to dryness. The residue was chromatographed over silica gel and was eluted with a 98-2 chloroform-methanol mixture to obtain 13 g of 5,5a,6,6a(RS),7,8,9,10a(RS)-octahydro-4-benzyl-7-(2-hydroxyethyl)-4H-indolo-[3,4-g,h][1,4]-benzoxazine which after crystallization from isopropyl ether melted at 108° C.

EXAMPLE 14

5,5a,6,6a(RS),7,8,9,10a(RS)-octahydro-4-benzyl-7-(2-chloroethyl)-4H-indolo-[3,4-g,h][1,4]-benzoxazine 7 ml of methane sulfonyl chloride were slowly added to a mixture of 11.5 g of the product of Example 13 in 100 ml of pyridine and the mixture was stirred at room temperature for 17 hours and was then poured into an ice-water mixture. The mixture was made alkaline with ammonium hydroxide solution and was extracted with methylene chloride. The organic phase was washed with water, dried and evaporated to dryness under reduced pressure. The residue was chromatographed over silica gel and was eluted with a 95-5 chloroform-methanol mixture to obtain 9.7 g of 5,5a,6,6a(RS),7,8,9,10a(RS)-octahydro-4-benzyl-7-(2-chloroethyl)-4H-indolo-[3,4-g,h][1,4]-benzoxazine melting at 112° C.

EXAMPLE 15

5,5a,6,6a(RS),7,8,9,10a(RS)-octahydro-7-(2-chloroethyl)-4H-indolo-[3,4-g,h][1,4]-benzoxazine Hydrogen was bubbled with stirring through a mixture of 0.37 g of the product of Example 14, 10 ml of acetic acid and 0.9 g of 10% palladized activated carbon for 3 hours and the mixture was filtered. The filter was washed with acetic acid and the filtrate was evaporated to dryness under reduced pressure. The residue was added to water and the mixture was made alkaline with 1 N sodium hydroxide solution. The mixture was extracted with methylene chloride and the organic phase was washed with water, dried and evaporated to dryness. The residue was chromatographed over silica gel and was eluted with a 95-5 chloroform-methanol mixture to obtain 0.2 g of 5,5a,6,6a(RS),7,8,9,10a(RS)-octahydro-7-(2-chloroethyl)-4H-indolo-[3,4-g,h][1,4]-benzoxazine melting at 112° C.

EXAMPLE 16

6,6a(RS),7,8,9,10a(RS)-hexahydro-7-(2-chloroethyl)-4H-indolo[3,4-g,h][1,4]-benzoxazine A mixture of 0.06 g of the product of Example 15, 4 ml of methylene chloride and 0.24 g of activated manganese dioxide was stirred under an inert atmosphere for 17 hours and was then filtered. The filter was rinsed with methylene chloride and the filtrate was evaporated to dryness. The residue was chromatographed over silica gel and was eluted with a 95-5 chloroform-methanol mixture to obtain 0.03 g of 6,6a(RS),7,8,9,10a(RS)-hexahydro-7-(2-chloroethyl)-4H-indolo[3,4-g,h][1,4]-benzoxazine melting at 132° C.

EXAMPLE 17

Tablets were prepared containing 2.5 mg of 6,6a(RS),7,8,9,10a(RS)-hexahydro-7-methyl-4H-indolo-[3,4-g,h][1,4]-benzoxazine hydrochloride or 0.1 mg of 6,6a(RS),7,8,9,10a(RS)-hexahydro-7-propyl-4H-indolo-[3,4-g,h][1,4]-benzoxazine hydrochloride or 2.5 mg of 5-bromo-6,6a(RS),7,8,9,10a(RS)-hexahydro-7-propyl-4H-indolo-[3,4-g,h][1,4]-benzoxazine hydrochloride and sufficient excipient of talc, starch, lactose and magnesium stearate for a final weight of 100 mg.

PHARMACOLOGICAL STUDY

A. Rotation behavior after unilateral injury of nigrostriatal bundle

The unilateral lesion was effected with male rats weighing about 220 g of unilateral injection into nigrostriatal dopaminergic bundle of 8 μg of 6-hydroxydopamine in a solution of 2 μg per μl by the method of Ungerstedt [Acta. Physiol. Scand., Vol. 82 (1971), supp. 367, p. 69–93]. In the animals, the direct dopaminergic agonits such as apomorphine administered generally induces a rotating behavior in the contralateral direction to the injured side. The test compounds were administered more than 5 weeks after the lesion and the rats were placed in an automatic rotometer which determined the number of rotations effected by each animal in 2 directions.

All the tested compounds were entrained at doses less than 1 mg/kg administered peritoneally the number of contralateral rotations and the duration as a function of the dose administered. The compound of Example 9 was particularly active in this regard and presented also at a dose of 0.02 mg/kg a very strong activity which was on the order of 1500 turns and was prolonged with a duration of 5 to 6 hours.

B. Antihypertensive Activity

The antihypertensive activity of the compound of Example 9 was determined on Beagle dogs weighing between 12 and 14 kg made hypertensive by wrapping the 2 kidneys with cellophane by the technique of Irvine H. Page [Science, Vol. 89 (1939), p. 273–274]. The test product was administered orally at doses of 1 and 10 mg/kg and the arterial pressure was measured on the tail by a pneumatic collar and with the aid of a piezo-electric pressure transducer. The pressure was measured before and 1,3,6 and 24 hours after the product administration and the percentage of arterial pressure variation after administration of the product was compared to the initial control pressure. The results are reported in Table I.

TABLE I

| Product of Example | Dose in mg/kg | % variation of arterial pressure-hours after administration | | | |
|---|---|---|---|---|---|
| | | 1 | 3 | 6 | 24 |
| 9 | 0.1 | −22 | −18 | −7 | −9 |

C. Antihypertensive Activity

The antihypertensive activity was studied on spontaneously hypertensive male rats of Wistar-Kyoto strain 20 weeks old weighing between 300 and 320 g. The test product was orally administered 48 hours after the placing of an intracarotidin catheter and the arterial pressure was measured on the rat's tail with a pneumatic collar and a piezo-electric pressure transducer. The pressure was determined before and 1,4 and 24 hours after the administration of the test product and the percent of variation was determined as in A. The results are reported in Table II.

TABLE II

| Product of Example | Dose in mg/kg | % arterial pressure variation after | | |
|---|---|---|---|---|
| | | 1 hr. | 4 hr. | 24 hr. |
| 9 | 1 | −17 | −14 | −3 |

D. Hypotensive Activity

The hypotensive activity was studied on male rats of the Wistar strain weighing about 300 g and anesthesized with nembutal (50 mg/kg-intraveinously). The test compound was administered intraveinously through the jugular vein and carotidine arterial pressure was measured before and after the test product administration. The arterial pressure difference were calculated as for Table I and the results are reported in Table III.

TABLE III

| Product of Example | Dose in mg/kg | % arterial pressure variation after minutes | | | |
|---|---|---|---|---|---|
| | | 1 | 5 | 10 | 30 |
| 9 | 0.1 | −40 | −61 | −59 | −54 |
| | 0.01 | −33 | −25 | −25 | −17 |
| 8 | 0.1 | −44 | −50 | −38 | −30 |
| | 0.01 | −37 | −28 | −24 | −3 |

D. Acute toxicity

The acute toxicity was determined on groups of mice who intrapenitoneally received the test compounds to determine the $DL_O$ dose or the maximum dose at which no mice were killed after 8 days. The $DL_O$ results for the products of Examples 3,6,8, 9 and 10 were between 80 and 100 mg/kg.

Various modifications of the products and processes of the invention may be made without departing from the spirit or scope thereof and it should be understood that the invention is intended to be limited only as defined in the appended claims.

What we claim is:

1. A compound selected from the group consisting of indolobenzoxazines of the formula

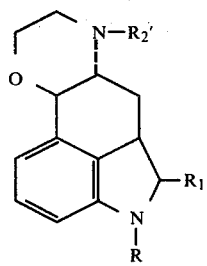

wherein R is selected from the group consisting of hydrogen, alkyl of 1 to 5 carbon atoms and optionally substituted aralkyl of 7 to 12 carbon atoms, $R_1$ is selected from the group consisting of hydrogen, chlorine and bromine, $R_2'$ is selected from the group consisting of hydrogen, optionally substituted alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts.

2. A compound of claim 1 wherein $R_2'$ is selected from the group consisting of hydrogen, alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts.

3. A compound of claim 2 wherein R is hydrogen and $R_2'$ is selected from the group consisting of hydrogen, alkyl of 1 to 5 carbon atoms and cycloalkylalkyl of 4 to 7 carbon atoms.

4. A compound of claim 2 wherein $R_1$ is hydrogen or bromine, R is hydrogen and $R_2'$ is hydrogen or alkyl of 1 to 5 carbon atoms.

5. A compound of claim 1 selected from the group consisting of 5,5a,6,6a(RS),7,8,9,10a(RS)-octahydro-7-propyl-4H-indolo-[3,4-g,h][1,4]-benzoxazine and its non-toxic, pharmaceutically acceptable acid addition salts.

6. A hypotensive and dopaminergic agonist compositions comprising a hypotensively and dopaminergically effective amount of at least one compound of claim 1 and an inert pharmaceutical carrier.

7. A composition of claim 6 wherein $R_2'$ is selected from the group consisting of hydrogen, alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts.

8. A composition of claim 6 wherein R is hydrogen and $R_2'$ is selected from the group consisting of hydrogen, alkyl of 1 to 5 carbon atoms and cycloalkylalkyl of 4 to 7 carbon atoms.

9. A composition of claim 6 wherein $R_1$ is hydrogen or bromine, R is hydrogen and $R_2'$ is hydrogen or alkyl of 1 to 5 carbon atoms.

10. A composition of claim 6 wherein the compound is selected from the group consisting of 5,5a,6,6a(RS),7,8,9,10a(RS)-octahydro-7-propyl-4H-indolo-[3,4-g,h][1,4-benzoxazine and its non-toxic, pharmaceutically acceptable acid addition salts.

11. A method of inducing hypotensive and dopaminergic agonist activity in warm-blooded animals comprising administering to warm-blooded animals an amount of at least one compound of claim 1 sufficient to cause hypotensive and dopaminergic agonist activity.

12. A method of claim 11 wherein $R_2'$ is selected from the group consisting of hydrogen, alkyl of 1 to 5 carbon atoms, cycloalkylalkyl of 4 to 7 carbon atoms, alkenyl and alkynyl of 3 to 7 carbon atoms and optionally substituted aralkyl of 7 to 12 carbon atoms and their non-toxic, pharmaceutically acceptable acid addition salts.

13. A method of claim 11 wherein R is hydrogen and $R_2'$ is selected from the group consisting of hydrogen, alkyl of 1 to 5 carbon atoms and cycloalkylalkyl of 4 to 7 carbon atoms.

14. A method of claim 11 wherein $R_1$ is hydrogen or bromine, R is hydrogen and $R_2'$ is hydrogen or alkyl of 1 to 5 carbon atoms.

15. A method of claim 11 wherein the compound is selected from the group consisting of 5,5a,6,6a(RS),7,8,9,10a(RS)-octahydro-7-propyl-4H-indolo-[3,4-g,h][1,4-benzoxazine and its non-toxic, pharmaceutically acceptable acid addition salts.

* * * * *